United States Patent [19]
Johns

[11] Patent Number: 5,840,052
[45] Date of Patent: Nov. 24, 1998

[54] ADHESIVE DRESSING APPLICATOR

[75] Inventor: Owen L. Johns, Madeira Beach, Fla.

[73] Assignee: Bertek, Inc., St. Albans, Vt.

[21] Appl. No.: 379,863

[22] Filed: Jan. 27, 1995

[51] Int. Cl.$^6$ .................................................. A61F 5/00
[52] U.S. Cl. .............................................. 602/54; 41/57
[58] Field of Search .................................. 604/140, 180; 602/41–43, 48, 52, 54, 57, 58, 59; 128/338, 889, DIG. 26

[56]           References Cited

U.S. PATENT DOCUMENTS

| | | |
|---|---|---|
| 2,897,961 | 5/1959 | Bush . |
| 2,969,144 | 5/1961 | Zackheim . |
| 4,265,234 | 5/1981 | Schaar . |
| 4,513,739 | 4/1985 | Johns . |
| 4,598,004 | 7/1986 | Heinecke ................................. 428/40 |
| 4,614,183 | 9/1986 | McCracken et al. . |
| 4,787,380 | 11/1988 | Scott . |
| 4,915,102 | 4/1990 | Kwiatek et al. . |
| 4,941,882 | 7/1990 | Ward et al. .............................. 604/180 |
| 5,042,466 | 8/1991 | McKnight . |
| 5,052,381 | 10/1991 | Gilbert et al. . |
| 5,074,293 | 12/1991 | Lott et al. . |
| 5,099,832 | 3/1992 | Ward .......................................... 602/57 |
| 5,106,629 | 4/1992 | Cartmell et al. ....................... 602/57 X |
| 5,209,718 | 5/1993 | McDaniel .................................. 602/53 |
| 5,372,589 | 12/1994 | Davis ...................................... 604/180 |

FOREIGN PATENT DOCUMENTS

| | | | |
|---|---|---|---|
| 998901 | 10/1976 | Canada ................................... 604/180 |
| 904632 | 8/1962 | United Kingdom . |

*Primary Examiner*—Richard J. Apley
*Assistant Examiner*—Kim M. Lee
*Attorney, Agent, or Firm*—Lerner, David, Littenberg, Krumholz & Mentlik

[57]           ABSTRACT

Wound dressings for application to a patient's skin are disclosed, including a dressing layer, a bio-compatible adhesive layer on one side thereof, a support layer on the other side of the dressing layer, the support layer extending around to the other side, and a separate protective layer on the adhesive side of the dressing layer, whereby the extended portion of the support layer is interposed between an edge of the dressing layer and the protective layer so as to facilitate removal and separation of the protective layer from the wound dressing while retaining the dressing layer on the support layer.

53 Claims, 3 Drawing Sheets

ADHESIVE DRESSING APPLICATOR

FIELD OF THE INVENTION

The present invention relates to wound dressings.

More particularly, the present invention relates to improved medical dressings for protecting external wounds on mammals, and particularly humans.

Still more particularly, the present invention relates to improved medical dressings which are easily applied.

BACKGROUND OF THE INVENTION

The field of wound dressings has seen development of a wide variety and great number of different products. Each of these wound dressing products is proposed as providing for protection and healing of various wounds. Thus, whether an accidental wound such as a burn or abrasion or a deliberate cut such as a surgical incision, or some dermatological skin disorder is to be treated, the number and variety of wound dressings has multiplied geometrically over the years.

Of particular significance are the types of wound dressings which are selectively permeable to oxygen and water vapor but which are impervious to liquids, infectious microorganisms and body salts. With these types of wound dressings, the problems of application are twofold; namely, because of the thin and filmy nature of these dressings, application without wrinkling becomes difficult; and, in addition, it is necessary to apply these dressings without contamination of the adhesive surface by the hand or glove of the person performing such application.

One particular type of wound dressing which has been developed includes various means for retarding removal of a release-coated layer from the adhesive-coated surface of the wound dressing or film, so that it can then be applied to the skin. These include products shown in patents such as my own prior U.S. Pat. No. 4,513,739, which utilizes release-retarding strips to facilitate application of the dressing to the wound area and prevent contamination. These can include, for example, plastic tape attached to the backing material by pressure-sensitive adhesives or the like. Other patents have approached this problem from a similar vein, including the use of various means to retard release of the release paper from the film itself. Patents of this type include Gilbert et al., U.S. Pat. No. 5,052,381, which includes a two-piece release sheet, as specifically shown in FIG. 2 thereof; McKnight, U.S. Pat. No. 5,042,466, which employs scoring or perforations to increase the adherence at the end portions thereof; Heinecke, U.S. Pat. No. 4,598,004, which utilizes delivery strips 12 and 13, which are affixed to the film edges by various means, such as heat-sealing and the like; and Lott et al., U.S. Pat. No. 5,074,293, which utilizes Mylar strips 22 and 23 to increase the resistance to peeling of the release liners therein.

Various other wound dressings have employed overall packaging systems which are intended to facilitate the sequential application of the film itself, and to maintain it within a sterile package before such use. For example, Bush, U.S. Pat. No. 2,897,961, and Zackheim, U.S. Pat. No. 2,969,144, disclose adhesive bandages within such systems. Furthermore, Scott, U.S. Pat. No. 4,787,380, discloses a delivery system for a medical dressing in which the dressing is cut out of the entire film backing sheet for application to the patient. In a more recent improvement in these devices, Kwiatek et al., U.S. Pat. No. 4,915,102, discloses an overall system for application of a film and/or active agent carrier, which includes provision for sequential opening and application of the film from portions thereof.

Various other such devices include additional means for application of the film, and employ a number of release liner portions for sequential removal of the release liner in various sections. These include, for example, Ward, U.S. Pat. No. 5,099,832, which is not only maintained within a sterile package, but which includes a two-part release liner, the first part formed into a V-shape, and the second part having a portion overlapping that V-shaped part. Furthermore, McCracken, U.S. Pat. No. 4,614,183, discloses a three-part release liner for application of the particular wound dressing therein.

It is therefore one object of the present invention to provide a novel wound dressing, which is not only simplified in its construction, but which can now be readily applied to wounds of various kinds in a manner which precludes contacting of the adhesive surface by the hands or gloves of the applying individual, while at the same time avoiding wrinkling of the film itself. It is yet another object of this invention to do so in a device in which the release liner is readily removed without in any way affecting retention of the film by a support or carrier layer, which can then be used to apply the film to the patient's skin.

SUMMARY OF THE INVENTION

These and other objects have now been realized by the discovery of a wound dressing including a dressing layer for application to the skin or mucosa of a host, the dressing layer having a first surface and a second surface, a bio-compatible adhesive layer on the first surface of the dressing layer, a support layer on the second surface of the dressing layer, the support layer including an extending portion extending around to the first surface of the dressing layer, and a separate protective layer on the first surface of the dressing layer, whereby the extending portion of the support layer is interposed between an edge portion of the first surface of the dressing layer and the separate protective layer to thereby facilitate removal and separation of the protective layer from the wound dressing while retaining the dressing layer on the support layer. Preferably, the separate protective layer is a single sheet or layer.

In accordance with a preferred embodiment of the wound dressing of the present invention, the dressing layer comprises a film layer. In another embodiment, however, the dressing layer can comprise a layer such as a non-woven fabric, a foam layer, or a polyolefin layer.

In accordance with one embodiment of the wound dressing of the present invention, the extending portion of the support layer is folded back upon itself to form a gripping portion for removal of the support layer from the dressing layer after the dressing layer has been applied to the skin or mucosa of the host.

In accordance with another embodiment of the wound dressing of the present invention, the extending portion of the support layer extends around only one edge of the dressing layer to the first surface thereof. Preferably, the extending portion of the support layer is interposed between an edge portion of the first surface of the dressing layer and a first end of the separate protective layer, and the separate protective layer includes a second free end separable from the wound dressing including the support layer.

In accordance with another embodiment of the wound dressing of the present invention, the adhesive layer can also include an additive, such as a drug component, a hydrocolloid, or an antibacterial agent.

In accordance with another embodiment of the wound dressing of the present invention, the extending portion of the support layer includes first and second extending portions of the support layer extending around a pair of opposing edges of the dressing layer to the first surface thereof. Preferably, the first and second extending portions of the support layer are each folded back upon themselves to form a pair of gripping portions for removal of the support layer from the dressing layer after the dressing layer has been applied to the skin or mucosa of the host.

In accordance with another embodiment of the wound dressing of the present invention, the dressing can include absorbant means affixed to the adhesive layer. Preferably, the absorbant means is an absorbant pad such as gauze, foam, or a hydrocolloid. In a preferred embodiment, the absorbent means has a predetermined configuration, and the separate protective layer includes an opening having a configuration designed to accommodate that predetermined configuration.

In accordance with another embodiment of the wound dressing of the present invention, there is provided a dressing layer for application to the skin or mucosa of a host, the dressing layer having a first surface, a second surface, a first edge, and a second edge, a bio-compatible adhesive layer on the first surface of the dressing layer, a support layer on the second surface of the dressing layer, the support layer including a first extending portion extending around the first edge to the first surface of the dressing layer, and a second extending portion extending around the second edge of the first surface of the dressing layer, and a protective layer on the first surface of the dressing layer, whereby the first and second extending portions of the support layer are interposed between the first and second edge portions of the first surface of the dressing layer and the protective layer to thereby facilitate removal of the protective layer while retaining the dressing layer on the support layer.

In a preferred embodiment of the wound dressing of the present invention, the dressing layer is once again a film layer. In another embodiment, however, the dressing layer can again be a layer such as a non-woven fabric, a foam layer, or a polyolefin layer.

In accordance with a preferred embodiment of this wound dressing of the present invention, the first and second extending portions of the support layer are folded back upon themselves to form first and second gripping portions for removal of the support layer from the dressing layer after the dressing layer has been applied to the skin or mucosa of the host.

In accordance with another embodiment of the wound dressing of the present invention where the dressing layer is a film layer, the support layer comprises an adhesively releasable surface with respect to the second surface of the film layer. In a preferred embodiment, the support layer includes the adhesively releasable surface on the entire surface thereof in contact with the second surface of the film layer. The support layer preferably includes the adhesively releasable surface on both surfaces thereof.

In accordance with another embodiment of the wound dressing of the present invention, the wound dressing comprises a dressing layer for application to the skin or mucosa of a host, the dressing layer having a first surface, a second surface, and a dressing layer fenestration for separating the dressing layer into a first dressing layer portion and a second dressing layer portion and for accommodating a catheter to be applied to the skin or mucosa of the host, a bio-compatible adhesive layer on the first surface of the dressing layer, a support layer on the second surface of the dressing layer, the dressing layer including an extending portion extending around to the first surface of the dressing layer at a location on the support layer corresponding to the dressing layer fenestration, the support layer including a support layer fenestration corresponding to the dressing layer fenestration, thereby dividing the extending portion of the support layer into a first extending portion and a second extending portion, and a separate protective layer on the first surface of the dressing layer, whereby the first and second extending portions of the support layer are interposed between edge portions of the first surface of the first and second dressing layer portions and the separate protective layer to thereby facilitate removal and separation of the protective layer from the wound dressing while retaining the dressing layer on the support layer and to further facilitate separate location of the first and second dressing layer portions with respect to the catheter.

In accordance with a preferred embodiment of this wound dressing of the present invention, the dressing layer once again is a film layer.

In accordance with another embodiment of this wound dressing of the present invention, the first and second extending portions of the support layer are folded back upon themselves to form gripping portions for removal of the support layer from the first and second dressing layer portions after the dressing layer has been applied to the skin or mucosa of the host.

In accordance with a preferred embodiment of this wound dressing of the present invention, the dressing layer includes a first dressing area including the first and second dressing layer portions and a second dressing area. In a preferred embodiment, the second dressing area is a water-vapor transmissible film area, preferably comprising polyurethane, and the first dressing area is preferably a non-woven fabric or a foam layer. In one embodiment, either a portion of or the entire first dressing area may consist of or be coated with a highly absorbent material, or a mixture of materials, such as pectin, algin, carboxymethyl cellulose, and the like, in such a fashion as to constitute an absorbent seal around the wound site, such as when criss-crossed under a tube or catheter oriented by the wound dressings hereof.

BRIEF DESCRIPTION OF THE DRAWINGS

The following detailed description of the present invention will be more readily appreciated with reference to the attached drawings, wherein.

DETAILED DESCRIPTION

Figure 1:
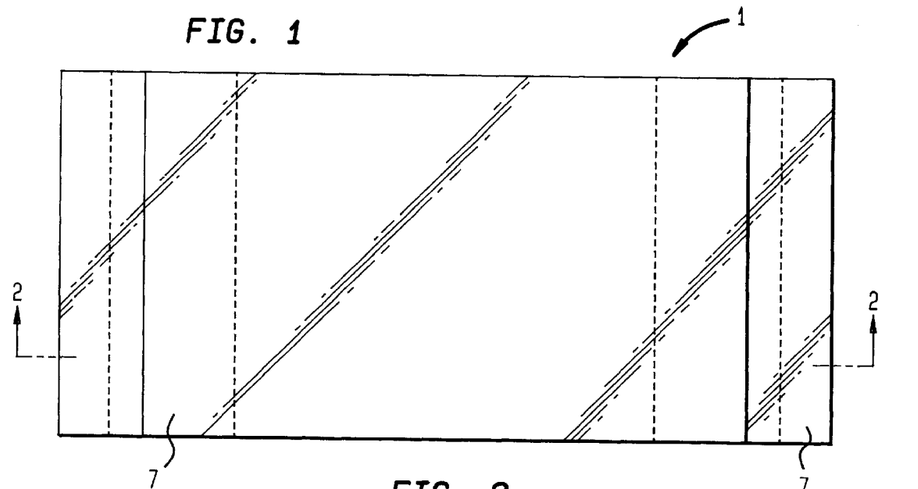
FIG. 1 is a top, plan view of a wound dressing according to the present invention.
Figure 8:
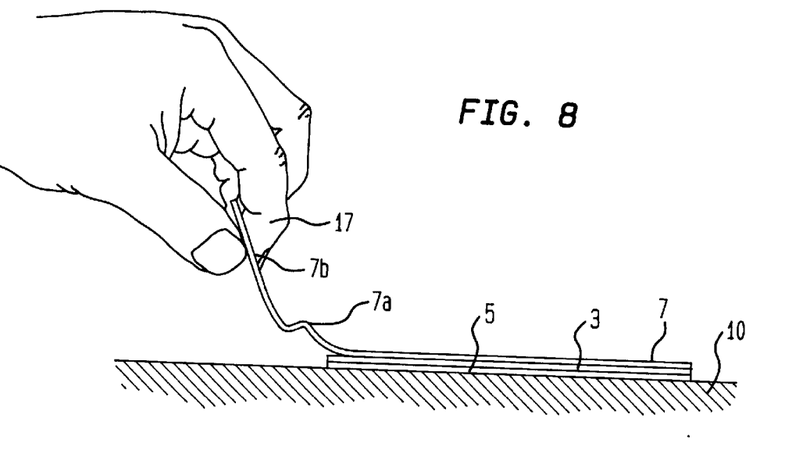
FIG. 8 is a side, elevational view of removal of the support layer from the wound dressing shown in FIGS. 3 and 7 after application to the patient's skin.
Figure 9:
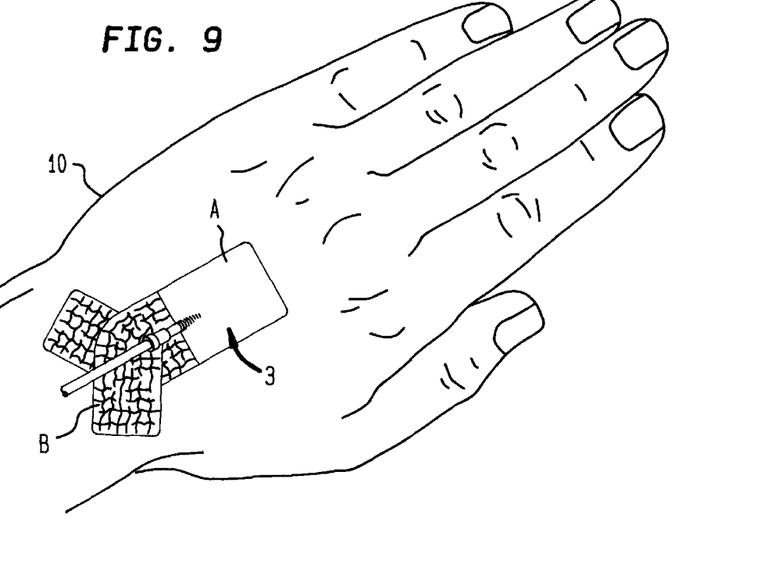
FIG. 9 is a top, elevational view of another wound dressing according to the present invention including a fenestration for application of a catheter tube applied to the patient's hand.

Referring to the drawings, in which like numerals refer to like elements thereof, FIG. 1 shows a wound dressing 1 which is intended to apply a dressing layer 3 to the skin or mucosa of the host or patient 10 (see FIGS. 8 and 9). The dressing layer 3 itself may consist of various types of layers, but will preferably comprise a moisture vapor permeable film produced from synthetic polymers which are capable of being formed into continuous films by casting, extrusion or other known film-making processes. On the other hand, the dressing layer 3 can also comprise a more substantial layer of spunbonded, wet laid or needle punched non-woven fabric. In addition, polyurethane, polyethylene, or other polyolefins, or other foam layers with various cell structures and densities can be used for some applications. Additionally, layer 3 can also be a laminate of several materials, such as a thin polyurethane film, a polypropylene spunbonded non-woven layer, and a perforated polyethylene film to prevent adhesion to a wound.

When the dressing layer 3 is a film layer, it is a material which would be extremely difficult, if not impossible, to handle by itself. This film layer 3, or "skin," is thus rather flimsy material which preferably allows air and moisture vapor to pass therethrough, but which will not permit the passage of bacteria or other undesired elements or materials. It is preferred that film layer 3 thus be composed of various thin, plastic materials, or it can comprise an extremely thin foil layer, or layer of other non-woven materials, most particularly it will comprise a material which is sufficiently thin and flexible to be conformable to the skin, and will thus generally have a film thickness of from about 0.5 to 5 mils, preferably thinner than about 2 mils, more preferably less than about 1.5 mils, and most preferably 1 mil or less. In addition, these film layers are preferably continuous in that they have no perforations or pores in the body contacting portion thereof.

These film layers 3 are preferably thermoplastic materials which are at least partially elastomeric in nature. They will therefore exhibit a high degree of elongation (preferably greater than about 130% elongation), and will thus exhibit excellent conformability characteristics without having the tendency to exhibit significant memory characteristics, although they will have some degree of recovery when stretched, for example. In terms of being breathable films, it is preferred that these materials in addition to permitting air to pass therethrough, will also permit moisture vapor to pass through them, at least more readily than is the case with materials such as polyethylene, for example. All of these film layers must be occlusive, at least with respect to particulates, in order to protect the wound, etc. However, their overall occlusive characteristics can then vary, depending upon the ultimate use intended for them in each particular case. In general, however, it is preferred that films be employed which are permeable to various glycols, such as polyethylene glycols, but rather occlusive films can also be employed in selected circumstances, including, for example, 1 and 2 mil layers of ethylene-vinyl acetate copolymers, or various nylon or polyester films. In addition, laminated or coated films could also be utilized, such as by employing a non-occlusive film such as those discussed above which is fully or partially selectively coated with an occlusive film.

The various thermoplastic films themselves can generally be produced with either a matte, glossy, or a clear surface, which is obtained by selection or modification of the surface of the chilling roller generally used downstream of the film extruder from which the film is extruded, and they can include various colors, such as skin color, as well as fillers, such as $TiO_2$, clay, or other such materials for the purpose of rendering the film opaque, and various organic additives, odor inhibitors, and/or various medications, etc. directly on the surface thereof.

From the commercial viewpoint, one of the most successful high moisture vapor permeable medical grade elastomeric films has been one of a series of products marketed by Bertek under the designation "Medifilm 800." These films are extruded from a class of elastomeric resins which are polyether block amides, commercially designated by the trademark PEBAX and sold by Atochem. The structure of these polymers can be generally represented by the formula:

in which PA represents a relatively rigid polyamide segment and PE represents a relatively soft polyether segment. In this manner the extruded film products have high strengths in terms of high tear and abrasion resistance and at the same time provide a high degree of comfort or conformability, as well as moisture vapor permeability. The physical properties of two typical medical grade PEBAX films having a thickness of 1 mil are set forth in TABLE 1 herein.

TABLE 1

| PROPERTIES | FILMS | |
| --- | --- | --- |
| | MEDIFILM 810 | MEDIFILM 827 |
| Tensile strength - psi (ASTM D-882) | 3120 | 2200 |
| % Elongation | 430 | 800 |
| Modulus @ 50% elongation | 1600 | 900 |
| Initial tear resistance - lbs. (ASTM D-1004) | 0.65 | 0.60 |
| MVTR - g/m2/24 hrs. (ASTM E-96) 37.8 C./90% R.H. | 1675 | 2200 |

In addition, other such film layers 3 can comprise thermoplastic polyurethanes which also meet the above requirements. These include such commercial polyurethane compositions as Dow Chemical Company's PELLETHANE, including its 2363-80AE grade thereof; K. J. Quinn's Q-THANE; B. F. Goodrich's ESTANE; Mobay Chemical Company's TXIN; and others. Furthermore, these film layers 3 can also comprise various polyesters, such as the copolymers of various cyclic polyesters including DuPont's HYTREL, including its 4056 grade thereof, and General Electric's LOMOD, both of which are copolymers of polyether prepolymers and polybutylene terephthalate and polyisobutyl terephthalate, respectively, as well as Eastman Chemical's PCCE. In addition, non-woven sheet materials or porous films having pore diameters below about 20 microns can also be employed for these purposes.

For the purpose of maintaining film layer 3 on the surface of the skin it is necessary to employ an adhesive layer 5 on one surface thereof. Adhesive layer 5 can be selected from any number of known commercially available medical grade adhesives. Such adhesives may be medical grade acrylics, silicon, polyisobutylene, or other applicable such adhesives, which can also be mixed with various agents, such as drugs, such as antibiotics and the like, hydrocolloids, and/or various antibacterial substances. Since the film layer 1 is preferably being applied to the skin, the adhesive layer should preferably be hypoallergenic. In any event, the particular selection of an adhesive for this purpose can include an acrylic copolymer adhesive such as Avery Chemical Company's AS-351 HSX, preferably at a coating weight of between about 25 and 35 g/m2. This pressure sensitive adhesive is a cross-linkable polymer which dries to provide a permanently tacky film having a total solids content of about 52%, a Brookfield viscosity (LVT/04/12 RPM @ 25° C.) of from about 15,000 to 25,000 cps and a weight per gallon of about 7.4 lbs. It can also be diluted with hexane or toluene to a desired solids and/or viscosity range, particularly for use in conventional coating equipment. Other such medical grade adhesives can include an acrylic pressure-sensitive adhesive sold by National Adhesives under the designation DURO-TAK 80-1054. This adhesive has a solids content of 47.5%, a viscosity of 3,000 cps, and a plasticity (Williams) of 2.9 mm. It is generally used with a solvent system including ethyl acetate, heptane, isopropyl alcohol and toluene. Another such adhesive is sold by Monsanto under the designation GELVA Multipolymer Emulsion 2484, and comprises a stable aqueous acrylic emulsion pressure-sensitive adhesive having a solids content of 59%, and a viscosity of 1,500-Z 300 cps. With these various adhesives the adhesion of this layer can be adjusted by the addition of a greater amount of cross-linking additives thereto and/or by utilizing different coating weights and/or viscosities therefor.

As mentioned above, because of the thin and flimsy nature of the film layer 3, it would be impossible to handle this material by itself if it were not used in connection with a support layer, in this case comprising support layer 7. However, such a support layer 7 is also used for the other non-film dressing layers of this invention, and, in fact, it is this support layer 7 which forms a critical element of the present invention, and which, although a single layer, performs a number of functions including and apart from this physical support of the dressing layer itself. Thus, support layer 7 appropriately creates a balance between adhering the dressing layer 1 to the support layer 7 itself and to the patient's skin in the manner shown in FIG. 8. Thus, if the degree of adhesion between the dressing layer 3 and the support layer 7 is too great, the dressing layer 3 will be pulled off the patient's skin 10 during removal of the support layer 7 in the manner shown. Reducing the degree of adhesion between the dressing layer 3 and the support layer 7, on the other hand, may cause the dressing layer 3 to be pulled away from the support layer 7 during removal of the protective layer 12 shown in FIG. 2. However, the method of providing for the appropriate balance in the present case includes providing the support layer 7 with an extending portion 7a which extends beyond the edge of the dressing layer 3, and this extending portion 7a extends around to the surface of the dressing layer 3 which includes adhesive layer 5. In this manner, the extending portion 7a of the support layer 7 is interposed between the dressing layer 3 and its associated adhesive layer 5 and the protective layer 12, at least at the leading edge portion of the dressing layer 3. This, in turn, will prevent the dressing layer 3 from being pulled off support layer 7 regardless of the level of adhesion between the dressing layer 3 and the support layer 7. Removal of the protective layer 12 simply cannot effect removal of the dressing layer 3 from the support layer 7 because of this configuration.

Figure 2:
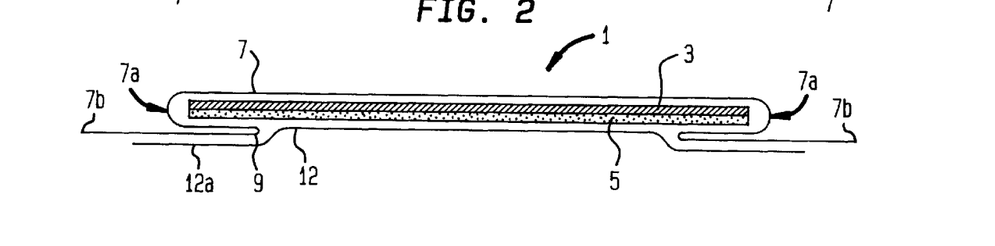
FIG. 2 is a side, cross-sectional view of the wound dressing shown in FIG. 1, taken along lines 2—2 thereof.
Figure 3:
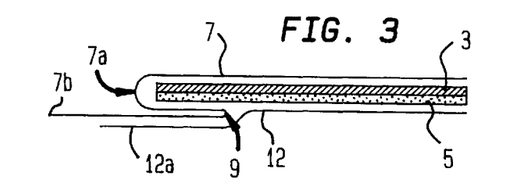
FIG. 3 is a side, cross-sectional view of another wound dressing according to the present invention.

In the embodiment of the present invention shown in FIG. 3, the extending portion 7a of the support layer 7 is present on only one side of the dressing layer 3. Even more preferably, the extending portion 7 includes a reverse fold 9 between the dressing layer 3 and the protective layer 12, which then extends outwardly to end portion 7b. In the embodiment shown in FIG. 2, however, the extension of support layer 7 takes place on both sides of the dressing layer 3, again in this case with the preferred reverse folds 9 on either end of the support layer 7 ending in end portions 7b at either end thereof.

The protective layer 12 is intended to initially, but only temporarily, be affixed to the underside of the dressing layer 3 in contact with adhesive layer 5 in the manner shown in FIGS. 2 and 3.

Both the support layer 7 and the protective layer 12 can therefore be made from numerous commercially available materials, including silicon- or teflon-coated release sheets. A large number of base polymers and paper compositions can be made into release sheets, including polyesters, polypropylene, polyethylene, styrene, unbleached kraft paper, and bleached kraft paper, both clay coated and uncoated. In particular, two suitable materials include No. 2226 polyester release liner and No. 2119 silicon-coated release paper produced by Bertek Medical Products. These materials can be particularly selected based upon the need in any particular case for transparency, stiffness, release force from the particular adhesive layer 5 involved, and the like. It is also possible that these support and/or protective layers can be laminates of two or more of these layers with each other, or with additional layers, such as foil, paper, various fabrics, and the like.

Figure 7:
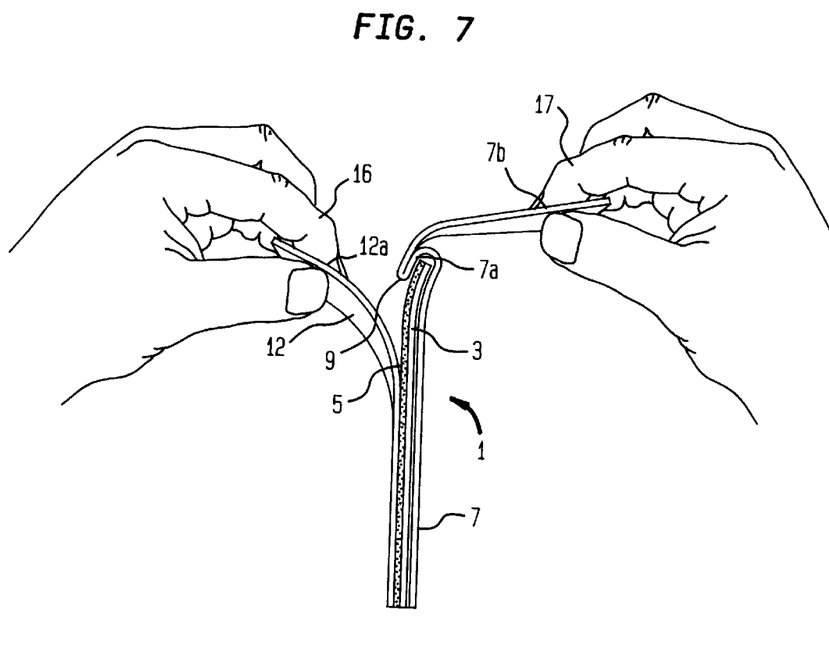
FIG. 7 is a side, elevational view demonstrating removal of the protective layer from the wound dressing shown in FIG. 3.

Referring again to the embodiment of the present invention shown in FIG. 3, application of this particular dressing layer 3 from wound dressing 1 can be seen in FIGS. 7 and 8. Thus, in FIG. 7 the protective layer 12 is initially removed by the user's grasping of end portion 12a with one hand 16 while at the same time grasping end portion 7b of the support layer 7 with the other hand 17. The protective layer 12 can then be stripped off of the wound dressing 1 without fear of removing the dressing layer 3 from the support layer 7 because of the interposition of the extending portion 7a including reverse fold area 9 between the dressing layer 3 and the protective layer 12. Subsequent to this removal of the protective layer 12, the dressing layer 3 and adhesive layer 5 can be placed on the appropriate location of the patient's skin 10, and the support layer 7 now readily removed by merely pulling the extended portion 7b of the support layer 7 with the user's hand 17 and lifting the support layer 7 off of the dressing layer 3 which then remains on the patient's skin 10.

Figure 4:
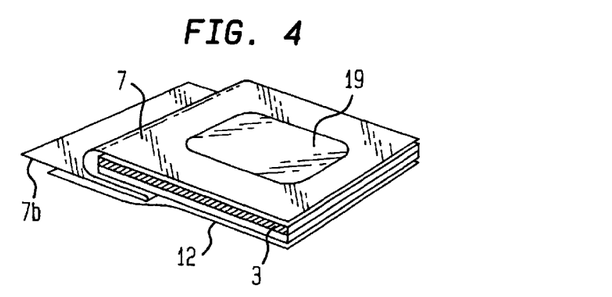
FIG. 4 is a perspective view of another wound dressing according to the present invention.

Another embodiment of the wound dressing of the present invention is shown in FIG. 4. In this case, the embodiment is similar to that shown in FIG. 3, except that the support layer 7 in this case includes an opening 19 to permit observation of the wound in the case where the support layer 7 is opaque while the dressing layer 3, such as a film layer, is transparent. Thus, the wound can be observed directly through opening 19 and transparent layer 3 therebeneath.

Figure 5:
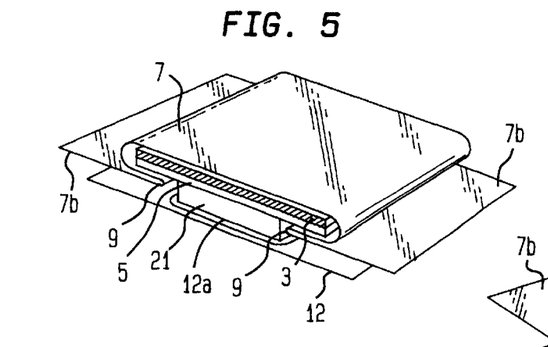
FIG. 5 is a perspective view of another wound dressing according to the present invention.

In the embodiment shown in FIG. 5 corresponds to the embodiment shown in FIG. 2, except that in this case the wound dressing includes an absorbent pad 21 which is attached to the adhesive surface 5 of the dressing layer 3. In this case, an opening 12a is provided in the protective layer 12 similar in configuration and size to the absorbent pad 21 so as to permit the remaining portion of protective layer 12 to remain in direct contact with the adhesive surface 5 of the dressing layer 3 entirely around absorbent pad 21, except, of course, for the area covered by the extending portion of support layer 7 as discussed above. As for the absorbent pad 21 itself, this can comprise various types of materials, including conventional gauze, various known types of foam materials, absorbtive hydrocolloid materials, and the like.

Figure 6:
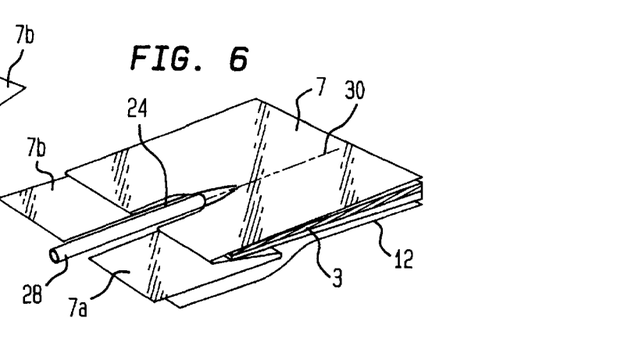
FIG. 6 is a top, perspective view of another wound dressing of the present invention including a fenestration for entry of a catheter tube.

Another important embodiment of the present invention is shown in FIGS. 6 and 9. In this case, again in an embodiment comparable to that of FIGS. 3 and 4, the fenestration 24 has been cut through the dressing layer 3 as well as the support layer 7. Additionally, support layer 7 has also been cut in a line parallel to a catheter 28 which has previously been applied to the patient's skin. This cut line 30 thus permits the dressing itself to be fit over catheter 28 as it is initially being applied to the patient's skin. Support layer 7 can then be slightly twisted under the catheter 28 and removed in sections to provide a sealed dressing layer 3 around and under the catheter 28. This can be more readily seen with reference to FIG. 9.

Figure 10:
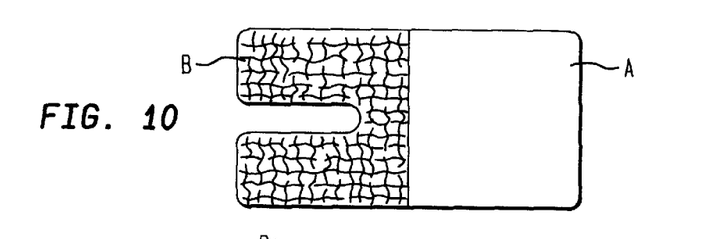
FIG. 10 is a top, elevational view of another embodiment of the wound dressing according to the present invention.

The embodiment shown in FIG. 9, however, includes a dressing layer 3 which is divided into two dressing areas A and B. In this preferred embodiment, dressing areas A and B can comprise different types of dressing layers in various combinations. In the embodiment shown in FIG. 9, for example, dressing area A comprises a film layer portion, while dressing area B, which includes two dressing layer portions divided by the fenestration means, includes a non-woven fabric or foam layer (i.e., a non-film layer). An absorbent material may be used, or a portion may be attached to dressing area B for purposes of sealing off the puncture site where catheter 28 penetrates the skin 10. This provides securement and support for the catheter 28, and protects the skin from pressure, abrasions and the like. This can be accomplished in a number of ways and in a number of variations. Thus, as shown in FIGS. 10–12, the configuration in which the dressing area A is a film layer and the dressing area B, including the fenestration, is a non-woven fabric area as in FIG. 9.

Figure 11:
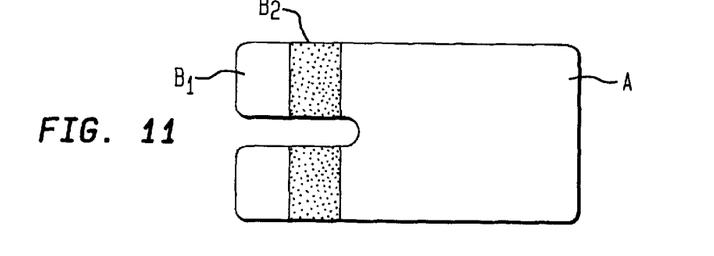
FIG. 11 is a top, elevational view of yet another embodiment of the wound dressing according to the present invention.
Figure 12:
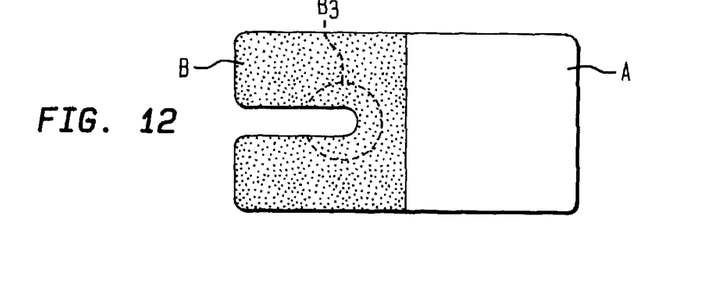
FIG. 12 is a top, elevational view of yet another embodiment of the wound dressing according to the present invention.

FIG. 11 shows a situation in which dressing area A again comprises a film layer, while portions of dressing area B comprise a film layer ($B_1$) and a layer of polyurethane foam ($B_2$). Finally, in FIG. 12, dressing area A again comprises a film layer, while dressing area B comprises a layer of polyurethane foam, with an absorbent material attached to the underside thereof, as shown by the broken line $B_3$.

Various other configurations such as dressings for heels and elbows are possible within the scope of the present invention, and these particular embodiments provide significant advantages when used in connection with the fenestration means for protecting the patient from undue abrasions and the like.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

I claim:

1. A wound dressing comprising a dressing layer for application to the skin or mucosa of a host, said dressing layer having a first surface and a second surface, a biocompatible adhesive layer on said first surface of said dressing layer, a support layer on said second surface of said dressing layer, said support layer including an extending portion extending around to said first surface of said dressing layer, and a separate protective layer on said first surface of said dressing layer, wherein said extending portion of said support layer is interposed between an edge portion of said first surface of said dressing layer and said separate protective layer to thereby facilitate removal and separation of said protective layer from said wound dressing while retaining said dressing layer on said support layer, and wherein said extending portion of said support layer is folded back upon itself to form a gripping portion for removal of said support layer from said dressing layer after said dressing layer has been applied to said skin or mucosa of said host, at least part of said extending portion being interposed between said folded gripping portion and said edge portion of said first surface.

2. The wound dressing of claim 1 wherein said dressing layer comprises a film layer.

3. The wound dressing of claim 1 wherein said separate protective layer comprises a single layer.

4. The wound dressing of claim 1 wherein said dressing layer comprises a layer selected from the group consisting of non-woven fabrics, foam, polyolefins, and mixtures thereof.

5. The wound dressing of claim 1 wherein said extending portion of said support layer extends around only one edge of said dressing layer to said first surface thereof.

6. The wound dressing of claim 5 wherein said extending portion of said support layer is interposed between an edge portion of said first surface of said dressing layer and a first end of said separate protective layer, and said separate protective layer includes a second free end separable from said wound dressing including said support layer.

7. The wound dressing of claim 1 wherein said adhesive layer includes an additive selected from the group consisting of a drug, a hydrocolloid, an antibacterial agent, and mixtures thereof.

8. The wound dressing of claim 1 wherein said extending portion of said support layer comprises first and second extending portions of said support layer extending around a pair of opposing edges of said dressing layer to said first surface thereof.

9. The wound dressing of claim 8 wherein said first and second extending portions of said support layer are each folded back upon themselves to form a pair of gripping portions for removal of said support layer from said dressing layer after said dressing layer has been applied to said skin or mucosa of said host.

10. The wound dressing of claim 2 wherein said support layer comprises an adhesively releasable surface with respect to said second surface of said film layer.

11. The wound dressing of claim 10 wherein said support layer includes said adhesively releasable surface on the entire surface thereof in contact with said second surface of said film layer.

12. The wound dressing of claim 11 wherein said support layer includes said adhesively releasable surface on both surfaces thereof.

13. The wound dressing of claim 1 wherein said support layer comprises a transparent sheet.

14. The wound dressing of claim 1 wherein said protective layer comprises silicon-coated release paper.

15. The wound dressing of claim 2 wherein said film layer is water-vapor transmissible.

16. The wound dressing of claim 2 wherein said film layer comprises polyurethane.

17. The wound dressing of claim 16 wherein said film layer is transparent.

18. The wound dressing of claim 1, including absorbent means affixed to said adhesive layer.

19. The wound dressing of claim 18, wherein said absorbent means comprises an absorbent pad selected from the group consisting of gauze, foam, hydrocolloids and mixtures thereof.

20. The wound dressing of claim 18 wherein said absorbent means has a predetermined configuration, and said separate protective layer includes an opening having a configuration designed to accommodate said predetermined configuration.

21. The wound dressing of claim 1 wherein said dressing layer and said support layer include fenestration means for accommodating a catheter to be applied to said skin or mucosa of said host.

22. A wound dressing comprising a dressing layer for application to the skin or mucosa of a host, said dressing layer having a first surface, a second surface, a first edge, and a second edge, a bio-compatible adhesive layer on said first surface of said dressing layer, a support layer on said second surface of said dressing layer, said support layer including a first extending portion extending around said first edge to said first surface of said dressing layer and a second extending portion extending around said second edge to said first surface of said dressing layer, and a protective layer on said first surface of said dressing layer, whereby said first and second extending portions of said support layer are interposed between said first and second edge portions of said first surface of said dressing layer and said protective layer to thereby facilitate removal of said protective layer while retaining said dressing layer on said support layer.

23. The wound dressing of claim 22 wherein said dressing layer comprises a film layer.

24. The wound dressing of claim 23, wherein said separate protective layer comprises a single layer.

25. The wound dressing of claim 23 wherein said dressing layer comprises a layer selected from the group consisting of non-woven films, foam, polyolefins, and mixtures thereof.

26. The wound dressing of claim 22 wherein said first and second extending portions of said support layer are folded back upon themselves to form first and second gripping portions for removal of said support layer from said dressing layer after said dressing layer has been applied to said skin or mucosa of said host.

27. The wound dressing of claim 26 wherein said support layer comprises an adhesively releasable surface with respect to said second surface of said film layer.

28. The wound dressing of claim 27 wherein said support layer includes said adhesively releasable surface on the entire surface thereof in contact with said second surface of said film layer.

29. The wound dressing of claim 28 wherein said support layer includes said adhesively releasable surface on both surfaces thereof.

30. The wound dressing of claim 22 wherein said support layer comprises a transparent sheet.

31. The wound dressing of claim 22 wherein said protective layer comprises silicon-coated release paper.

32. The wound dressing of claim 23 wherein said film layer is water-vapor transmissible.

33. The wound dressing of claim 23 wherein said film layer comprises polyurethane.

34. The wound dressing of claim 33 wherein said film layer is transparent.

35. The wound dressing of claim 22 wherein said dressing layer and said support layer include fenestration means for accommodating a catheter to be applied to said skin or mucosa of said host.

36. The wound dressing of claim 23 including absorbent means affixed to said adhesive layer.

37. The wound dressing of claim 36 wherein said absorbent means comprises an absorbent pad selected from the group consisting of gauze, foam, hydrocolloids, and mixtures thereof.

38. The wound dressing of claim 36 wherein said absorbent means has a predetermined configuration, and said separate protective layer includes an opening having a configuration designed to accommodate said predetermined configuration.

39. A wound dressing comprising a dressing layer for application to the skin or mucosa of a host, said dressing layer having a first surface, a second surface, and a dressing layer fenestration for separating said dressing layer into a first dressing layer portion and a second dressing layer portion and for accommodating a catheter to be applied to said skin or mucosa, a bio-compatible adhesive layer on said first surface of said dressing layer, a support layer on said second surface of said dressing layer, said support layer including an extending portion extending around to said first surface of said dressing layer at a location on said support layer corresponding to said dressing layer fenestration, said support layer including a support layer fenestration corresponding to said dressing layer fenestration, thereby dividing said extending portion of said support layer into a first extending portion and a second extending portion, and a separate protective layer on said first surface of said dressing layer, whereby said first and second extending portions of said support layer are interposed between edge portions of said first surface of said first and second dressing layer portions and said separate protective layer to thereby facilitate removal and separation of said protective layer from said wound dressing while retaining said dressing layer on said support layer, and to further facilitate separate location of said first and second dressing layer portions with respect to said catheter.

40. The wound dressing of claim 39 wherein said dressing layer comprises a film layer.

41. The wound dressing of claim 39 wherein said first and second extending portions of said support layer are folded back upon themselves to form gripping portions for removal of said support layer from said first and second dressing layer portions after said dressing layer has been applied to said skin or mucosa of said host.

42. The wound dressing of claim 40 wherein said support layer comprises an adhesively releasable surface with respect to said second surface of said film layer.

43. The wound dressing of claim 42 wherein said support layer includes said adhesively releasable surface on the entire surface thereof in contact with said second surface of said film layer.

44. The wound dressing of claim 43 wherein said support layer includes said adhesively releasable surface on both surfaces thereof.

45. The wound dressing of claim 39 wherein said support layer comprises a transparent sheet.

46. The wound dressing of claim 39 wherein said protective layer comprises silicon-coated release paper.

47. The wound dressing of claim 39 wherein said dressing layer comprises a first dressing area including said first and second dressing layer portions and a second dressing area.

48. The wound dressing of claim 47 wherein said second dressing area comprises a water-vapor transmissible film area.

49. The wound dressing of claim 48 wherein said second dressing area comprises polyurethane.

50. The wound dressing of claim 49 wherein said second dressing area is transparent.

51. The wound dressing of claim 47 wherein said first dressing area comprises a non-woven fabric.

52. The wound dressing of claim 47 wherein said first dressing area comprises a foam layer.

53. The wound dressing of claim 47 wherein said first dressing area comprises an absorbent material.

* * * * *

UNITED STATES PATENT AND TRADEMARK OFFICE
CERTIFICATE OF CORRECTION

PATENT NO. : 5,840,052
DATED : November 24, 1998
INVENTOR(S) : Johns

It is certified that error appears in the above-identified patent and that said Letters Patent is hereby corrected as shown below:

Column 12, line 3, "23" should read --22--

Signed and Sealed this

Thirtieth Day of March, 1999

Attest:

Q. TODD DICKINSON

*Attesting Officer*    *Acting Commissioner of Patents and Trademarks*